United States Patent
Qian

(10) Patent No.: US 9,815,823 B2
(45) Date of Patent: *Nov. 14, 2017

(54) CARBAZOLE KETOXIME ESTER HIGH-PHOTOSENSITIVITY PHOTOINITIATOR

(71) Applicant: CHANGZHOU TRONLY ADVANCED ELECTRONIC MATERIALS CO., LTD., Changzhou (CN)

(72) Inventor: Xiaochun Qian, Changzhou (CN)

(73) Assignee: CHANGZHOU TRONLY ADVANCED ELECTRONIC MATERIALS CO., LTD., Changzhou (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/648,120

(22) PCT Filed: Jan. 26, 2014

(86) PCT No.: PCT/CN2014/071445
§ 371 (c)(1),
(2) Date: May 28, 2015

(87) PCT Pub. No.: WO2014/121701
PCT Pub. Date: Aug. 14, 2014

(65) Prior Publication Data
US 2015/0307481 A1  Oct. 29, 2015

(30) Foreign Application Priority Data

Feb. 8, 2013 (CN) .......................... 2013 1 0050577

(51) Int. Cl.
| | |
|---|---|
| C07D 209/86 | (2006.01) |
| C07D 409/06 | (2006.01) |
| C07D 405/06 | (2006.01) |
| C08F 2/50 | (2006.01) |
| C08F 2/48 | (2006.01) |

(52) U.S. Cl.
CPC ......... C07D 409/06 (2013.01); C07D 209/86 (2013.01); C07D 405/06 (2013.01); C08F 2/48 (2013.01); C08F 2/50 (2013.01)

(58) Field of Classification Search
CPC ... C07D 209/86; C07D 409/06; C07D 405/06
USPC ................................................. 548/441, 446
See application file for complete search history.

(56) References Cited

U.S. PATENT DOCUMENTS

| | | | |
|---|---|---|---|
| 9,383,480 B2 * | 7/2016 | Qian ................. | G02B 1/04 |
| 2003/0036006 A1 | 2/2003 | Feke et al. | |
| 2009/0027608 A1 | 1/2009 | Nakamura et al. | |

FOREIGN PATENT DOCUMENTS

| | | | | |
|---|---|---|---|---|
| CN | 101354532 A | 1/2009 | | |
| CN | 101508744 A | 8/2009 | | |
| CN | 101565472 A | 10/2009 | | |
| CN | 101891845 A | 11/2010 | | |
| CN | 101923287 A | 12/2010 | | |
| CN | 102020727 A | * 4/2011 | .......... | C07D 209/86 |
| CN | 102375337 A | 3/2012 | | |
| CN | 102478766 A | * 5/2012 | | |
| CN | 102492060 A | 6/2012 | | |
| CN | 102645845 A | 8/2012 | | |
| CN | 102778814 A | 11/2012 | | |
| CN | 103130919 A | 6/2013 | | |
| CN | 103293855 A | 9/2013 | | |
| CN | 103389621 A | 11/2013 | | |
| EP | 2 407 456 A1 | 1/2012 | | |
| EP | 2 433 927 A1 | 3/2012 | | |
| JP | 2000-256565 A | 9/2000 | | |
| JP | 2010-184880 A | 8/2010 | | |
| WO | 2010/102502 A1 | 9/2010 | | |
| WO | 2010/133077 A1 | 11/2010 | | |
| WO | 2012/068879 A1 | 5/2012 | | |

OTHER PUBLICATIONS

Chinese First Office Action of corresponding Chinese Patent Application No. 201310050577.9 with English translation (8 pages) dated Apr. 11, 2014.
Chinese Second Office Action of corresponding Chinese Patent Application No. 201310050577.9 with English translation (4 pages) dated Sep. 17, 2014.
Chinese Third Office Action of corresponding Chinese Patent Application No. 201310050577.9 with English translation (4 pages) dated Oct. 27, 2014.
Song et al., "Synthesis of a Photoinitiator OXE—2," *Fine Chemicals* (w/English abstract) (4 pages) (Oct. 2009).
Chinese Office Action, dated Sep. 23, 2014, for Chinese Application No. 201310187435.7, 11 pages. (with English Translation).

(Continued)

*Primary Examiner* — Matthew Coughlin
*Assistant Examiner* — Sagar Patel
(74) *Attorney, Agent, or Firm* — Seed IP Law Group LLP

(57) ABSTRACT

A carbazolyl ketoxime ester type photoinitiator having a structure represented by the formula (I) is disclosed. This photoinitiator has excellent application performance and extremely high photosensitive property, and in particular under exposure lamp sources such as LED, LDI, etc., and it exhibits very high photosensing activity, which is obviously superior to the current products.

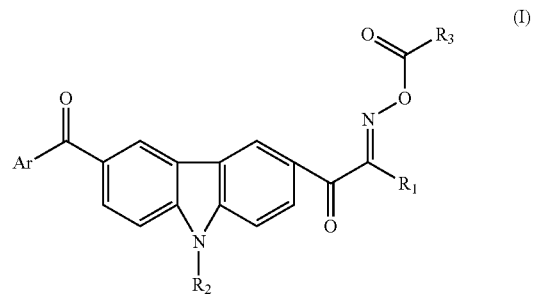

6 Claims, No Drawings

(56) References Cited

OTHER PUBLICATIONS

International Search Report, dated May 20, 2014, for International Application No. PCT/CN2014/071443, 6 pages.
Written Opinion, dated May 20, 2014, for International Application No. PCT/CN2014/071443, 8 pages. (with Partial English Translation).

* cited by examiner

CARBAZOLE KETOXIME ESTER HIGH-PHOTOSENSITIVITY PHOTOINITIATOR

FIELD OF THE INVENTION

This invention relates to the technical field of photoinitiators, and particularly relates to a carbazolyl ketoxime ester type photoinitiator.

BACKGROUND OF THE INVENTION

Photo-curing refers to a process in which a matrix of a monomer, an oligomer, or a polymer is cured under the light induction, and this technology has a wide use in modern micro-electronic technologies, for example, photo-cured inks, packaging of liquid crystal panels, photosensitive printing plates, color filters, photoresists, and the like. The key point of photo-curing technology lies in photo-curable polymerizable monomers and suitable photoinitiators. Under the irradiation of a light source having a certain wavelength, a photoinitiator generates an active group, which excites an unsaturated group in a polymerizable monomer so that a polymerization reaction occurs, and thereby leads to the curing of the material.

The photoinitiator is a paramount factor which affects the photosensitive property of a photo-curable composition (i.e., a photosensitive composition). At present, there have been a number of studies and reports concerning the photoinitiators. However, these photoinitiators generally have a low photosensing activity, and has serious limit in terms of the type of the applicable light sources. Most of them are only suitable for ultraviolet excitation. For example, there exists oxime ester type photoinitiators, such as a carbazolyl oxime ester type photoinitiator disclosed in CN101508744A, a commercially available oxime ester type photoinitiator OXE-02, a ketoxime ester type photoinitiator disclosed in CN101565472A, a commercially available ketoxime ester type photoinitiator OXE-01, etc., all of which only meet the requirement for applications using a mercury lamp (including high-pressure, middle-pressure, and low-pressure mercury lamps) as the exposure source.

Along with the increase of awareness and requirement for environment and safety, as well as the development of the photopolymerization technology, exposure lamp sources being low-energy, high-safety, energy-saving, and environmentally friendly such as LED, LDI, etc., have become a trend in the application and the development of technologies in this field. Under this situation, it has important practical and economic meanings to research and develop a photoinitiator capable of matching low-energy and long-wavelength-output exposure sources such as LED, LDI, etc. At present, none of the current photoinitiators may well match the exposure sources such as LED, LDI, etc., and a low photosensitivity (i.e., photosensing activity) is exhibited.

In view of this, this invention discloses a carbazolyl ketoxime ester type photoinitiator, this type of photoinitiator may not only match the light sources of mercury lamps, but also may well match low-energy and long-wavelength-output exposure sources such as LED, LDI, etc., and has a very high photosensitivity.

SUMMARY OF THE INVENTION

An object of the present invention is to provide a novel carbazolyl ketoxime ester type photoinitiator, which has very excellent photosensitive property and exhibits very high photosensitivity under the exposure sources such as LED, LDI, etc.

In order to achieve the technical effect described above, this invention employs the following technical solutions:

a carbazolyl ketoxime ester type photoinitiator, having a structure represented by the formula (I) of:

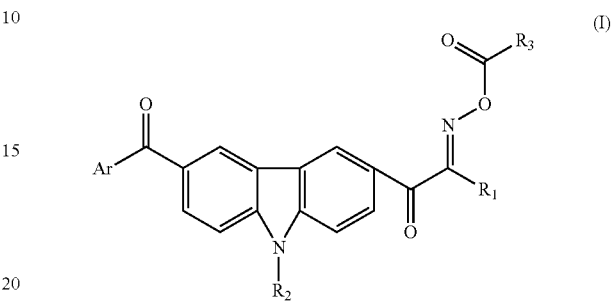

$R_1$ is

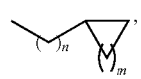

$n = 1\sim5, m = 1\sim6$;

$R_2$ is a $C_1\sim C_{20}$ linear or branched alkyl group;

$R_3$ is a $C_1\sim C_{10}$ alkyl group, a $C_3\sim C_8$ cycloalkyl group, or a cycloalkylalkyl group consisting of a $C_1\sim C_4$ alkyl group and a $C_3\sim C_8$ cycloalkyl group, or a phenyl group optionally substituted by an alkyl group (i.e., the substituent may be present or absent);

Ar is a S or O-containing heterocyclic group having an optional substituent (i.e., the substituent may be present or absent), or a substituted aryl group having an O, S, or N atom-containing substituent.

Further, in the carbazolyl ketoxime ester type photoinitiator compound represented by the formula (I) described above, in $R_1$, preferably n=1 or 2 and m=3 or 4.

$R_2$ is preferably a $C_1\sim C_5$ linear or branched alkyl group, more preferably methyl, ethyl, n-propyl, or n-butyl, and particularly preferably ethyl.

$R_3$ is preferably a $C_1\sim C_3$ linear or branched alkyl group, and more preferably methyl.

In Ar, the S or O-containing heterocyclic group having an optional substituent preferably has 0~2 substituents, particularly 0~2 methyl or ethyl groups; and the S or O-containing heterocyclic group is preferably furanyl or thienyl. The O, S, or N atom-containing substituent in the substituted aryl group is preferably an alkylthio group, an alkoxy group, an alkylamino group, a piperazinyl group, a morpholinyl group, and the like.

Furthermore, in the carbazolyl ketoxime ester type compound represented by the formula (I) described above, Ar is preferably selected from the following structures of:

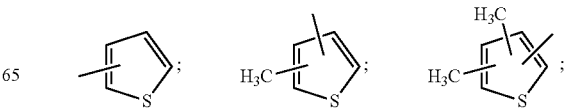

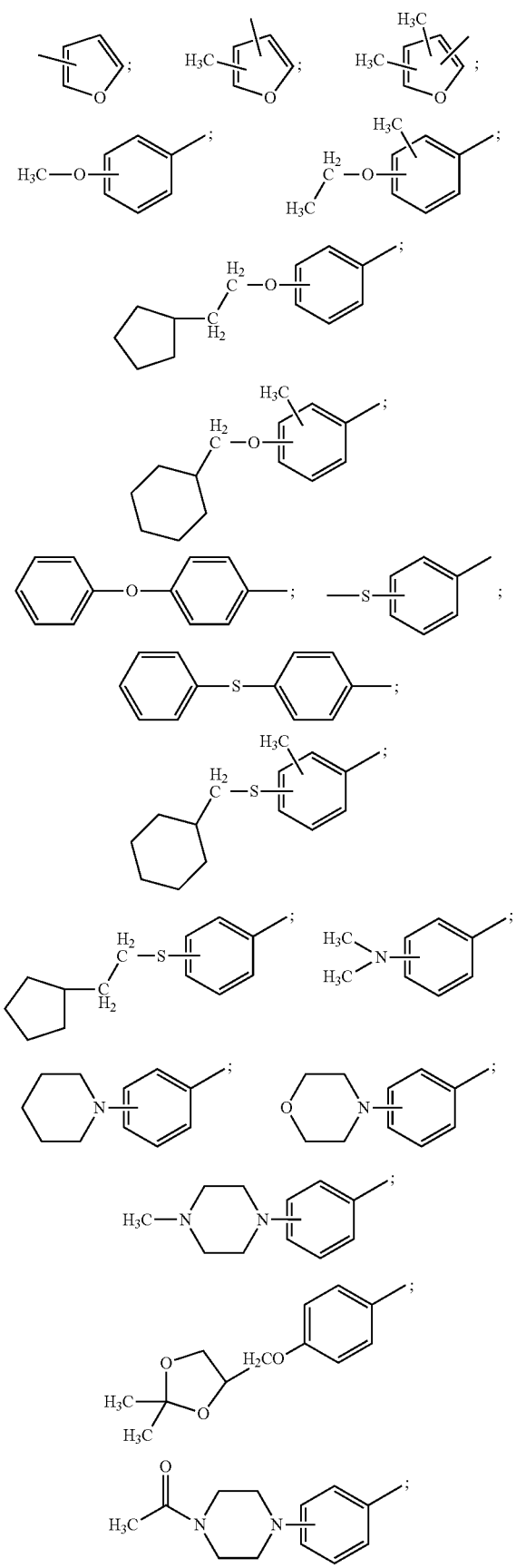

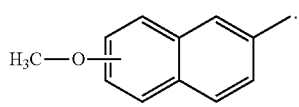

The object of the present invention is to further provide a method for preparing the carbazolyl ketoxime ester type photoinitiator represented by the formula (I) described above, using carbazole as a starting raw material, and comprising the steps of:

(1) a substitution reaction, in which carbazole is dissolved in an organic solvent and is subjected to a substitution reaction with a bromoalkane $R_2$—Br to obtain an intermediate a, i.e., 9-$R_2$-carbazole, wherein the reaction process thereof is as follows:

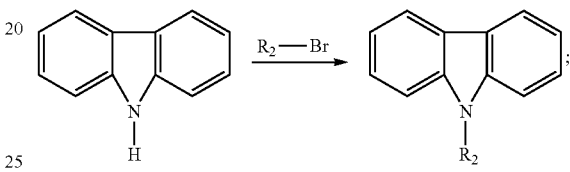

(2) an acylation reaction, in which the intermediate a (9-$R_2$-carbazole) is dissolved in an organic solvent and is subjected to an acylation reaction under the catalysis of aluminum trichloride to obtain an intermediate b, i.e., 3-$R_1$-acetyl-6-Ar-acyl-9-$R_2$-carbazole, wherein the reaction process thereof is as follows:

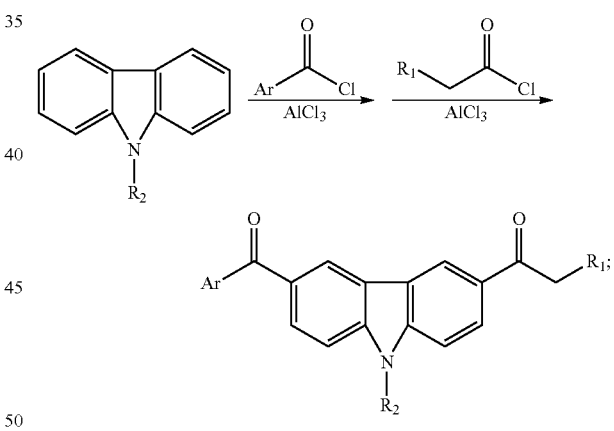

(3) an oxidation reaction, in which the prepared intermediate b (3-$R_1$-acetyl-6-Ar-acyl-9-$R_2$-carbazole) is subjected to an oxidation reaction to prepare an intermediate c, i.e., 1-(6-Ar-acyl-9-$R_2$-carbazol-3-yl)-2-$R_1$-1,2-dione-2-oxime, wherein the reaction process thereof is as follows:

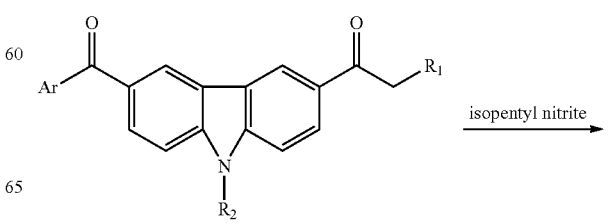

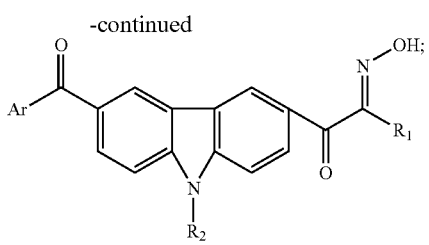

(4) an esterfication reaction, in which an esterfication reaction is performed between the prepared intermediate c (1-(6-Ar-acyl-9-$R_2$-carbazol-3-yl)-2-$R_1$-1,2-dione-2-oxime) and a $R_3$-formic anhydride or a $R_3$-formyl chloride to prepare the object product, i.e., the carbazolyl ketoxime ester type photoinitiator represented by the formula (I), wherein the reaction process thereof is as follows:

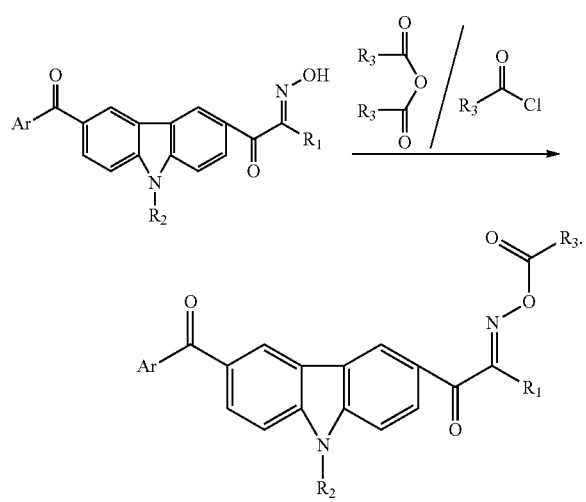

All of the raw materials used in the preparation method described above are compounds which are known in the prior art, commercially available, or prepared by known synthetic methods, and the reaction principle of each step of the reaction will be easily understood by the person skilled in the art.

In addition, the object of the present invention is to further provide an intermediate compound (i.e., the intermediate c described above) used for preparing the carbazolyl ketoxime ester type photoinitiator represented by the formula (I) described above, having the following structure of

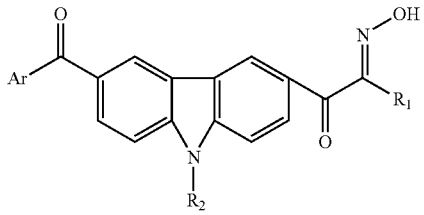

wherein the definitions of $R_1$, $R_2$ and Ar, as described above, are the same as those in the formula (I).

The carbazolyl ketoxime ester type compound represented by the formula (I) of this invention may be used as a photoinitiator in a photosensitive (photo-curable) composition, and has particularly excellent photosensitive property. Herein, other components in the photosensitive composition are not particularly limited and may be the components which are well known and commonly used in the art (see, for example, the content disclosed by CN101059655A, which is incorporated herein by reference in its entirety), for example, the photopolymerizable acrylic resins.

Advantageous Effects of the Invention: the carbazolyl ketoxime type photoinitiator of this invention has excellent application performance and extremely high photosensitive property, and in particular under the exposure lamp sources such as LED, LDI, etc., it exhibits very high photosensing activity, which is obviously superior to the current photoinitiators such as commercially available Irgacure369, OXE-01, and the like, and is also superior to the carbazolyl ketoxime ester type photoinitiator disclosed in CN101565472A. Meanwhile, the production method of this invention is simple, does not produce polluted wastes in the process of production, has high product purity, and is suitable for industrial production.

DETAILED DESCRIPTION OF THE INVENTION

Hereafter, this invention will be illustrated in conjunction with specific Examples, but it is not to be understood that the scope of this invention is limited thereto.

PREPARATION EXAMPLE

Example 1

The preparation of 1-[6-(2-thiophenecarbonyl)-9-ethyl-carbazol-3-yl]-3-cyclopentyl-propan-1,2-dione-2-oxime acetate shown as below

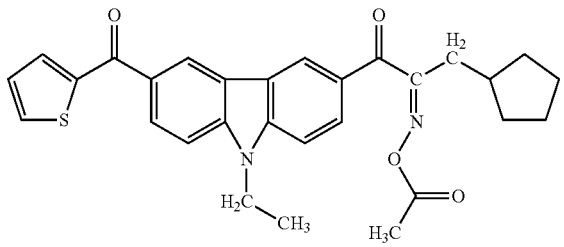 [SMILES: CCn1c2ccc(C(=O)/C(CC3CCCC3)=N\OC(C)=O)cc2c2cc(C(=O)c3cccs3)ccc21]

Step 1: The preparation of 9-ethylcarbazole

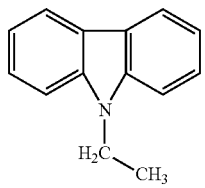

40 g of carbazole, 1.5 g of tetraethylammonium bromide, and 200 mL of toluene were added to a 500 mL four-neck flask, and 140 g of a freshly prepared 50% aqueous NaOH solution was added with stirring, then 31.2 g of bromoethane was dripped within about 30 min, and then a reaction was performed with heating reflux for 6 h. After cooling to room temperature, the water layer is separated and removed, the material liquid layer was washed with water for 3 times, followed by drying with anhydrous MgSO₄, suction filtration, and concentration under reduced pressure to remove the solvent, and the residue was recrystallized with absolute ethanol to obtain 70 g of a white needle-like crystal with a yield of 75% and a relative purity of 99%.

Step 2: The preparation of 3-(3-cyclopentylpropionyl)-6-(2-thiophenecarbonyl)-9-ethylcarbazole

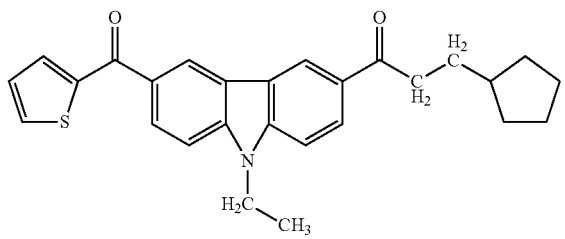 [SMILES: CCn1c2ccc(C(=O)CCC3CCCC3)cc2c2cc(C(=O)c3cccs3)ccc21]

30 g of 9-ethylcarbazole, 21.6 g of AlCl₃ (finely ground), and 150 mL of dichloromethane were added to a 500 mL four-neck flask and stirred, and argon gas was supplied for protection, followed by cooling with ice bath. When the temperature decreased to 0° C., a mixed liquid of 23.2 g of 2-thienyl formyl chloride and 21 g of dichloromethane begun to be dripped, while the temperature was controlled at 10° C. or less, and the dripping was finished in about 1.5 h. Stirring was continued for 2 h, followed by addition of 21.6 g of AlCl₃ (finely ground), a mixed liquid of 27.2 g of cyclopentylpropionyl chloride and 20 g of dichloromethane, while the temperature was controlled at 10° C. or less, and the dripping was finished in about 1.5 h. When the temperature was increased to 15° C., stirring was continued for 2 h, and the reaction was stopped. The reaction liquid was poured into diluted hydrochloric acid formulated with 400 g of ice and 65 mL concentrated hydrochloric acid, the material liquid in the lower layer was separated using a separation funnel, and the upper layer was extracted with 50 mL of dichloromethane. The extract and the material liquid were combined with, followed by washing with NaHCO₃ solution formulated with 10 g of NaHCO₃ and 200 g of water, and were further washed with 200 mL water for 3 times until pH value become neutral. Water was removed by drying with 30 g of anhydrous MgSO₄, and dichloromethane was evaporated by rotation. After evaporation, the crude product in a rotary evaporation flask presented the form of a solid powder and was poured into 200 mL petroleum ether, which was evaporated under normal pressure to obtain a light yellow powdery solid upon suction filtration, and a product of 46.2 g was obtained after drying in an oven at 70° C. for 2 h, with a yield of 70% and a purity of 95.2%.

Step 3: The preparation of 1-[6-(2-thiophenecarbonyl)-9-ethylcarbazol-3-yl]-3-cyclopentyl-propan-1,2-dione-2-oxime

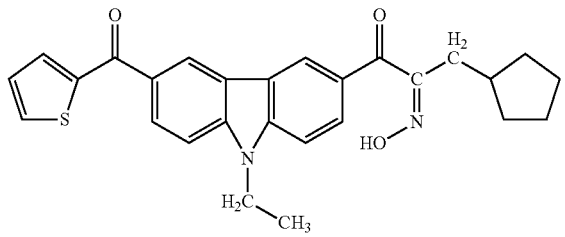 [SMILES: CCn1c2ccc(C(=O)/C(CC3CCCC3)=N\O)cc2c2cc(C(=O)c3cccs3)ccc21]

19.1 g of the product of step 2, 100 mL tetrahydrofuran, 19 g of concentrated hydrochloric acid, and 8 g of isopentyl nitrite were added to a 250 mL four-neck flask, stirred at normal temperature for 5 h, and then the reaction is stopped. Materials were poured into a 2000 mL beaker and stirred after 1000 mL water was added, and 200 g of dichloromethane was used for extraction. The extract was dried by adding 50 g anhydrous MgSO₄, followed by suction filtration. The filtrate was removed by rotary evaporation under reduced pressure, and an oily viscous substance was obtained in a rotary bottle. The viscous substance was poured into 150 mL petroleum ether and was precipitated with stirring, followed by suction filtration, a yellow powdery solid was obtained, and after drying at 70° C. for 5 h, a product of 14.8 g was obtained with a yield of 74% and a relative purity of 95%.

The structure of the product was determined by hydrogen nuclear magnetic resonance spectroscopy, and the specific characteristic result is as follows:

¹H-NMR (CDCl₃, 500 MHz): 1.468~1.497 (3H, t, —CH₃), 1.537~1.893 (9H, m, cyclopentane), 2.706~2.722 (2H, d, —CH₂—), 4.401~4.444 (2H, q, —CH₂—), 7.285~8.542 (9H, m, aromatic ring).

Step 4: The preparation of 1-[6-(2-thiophenecarbonyl)-9-ethylcarbazol-3-yl]-3-cyclopentyl-propan4,2-dione-2-oxime acetate 14.8 g of the product of step 3 and 100 g dichloromethane were added to a 250 mL four-neck flask and were stirred at room temperature for 5 min, and then acetic anhydride was dripped within about 30 min. Stirring was continued for 2 h, and then 5% NaHCO₃ was added to adjust pH value to neutral. Layer separation was performed by a separation funnel, followed by washing twice with 200 mL water and drying with 50 g anhydrous MgSO₄, and the solvent was evaporated by rotation to obtain a viscous liquid. Recrystallisation by methanol was performed to obtain a beige solid powder, which was filtered and dried at 70° C. for 5 h to obtain a product of 11 g with a purity of 98%.

The structure of the product was determined by hydrogen nuclear magnetic resonance spectroscopy, and the specific characteristic result is as follows:

¹H-NMR (CDCl₃, 500 MHz): 1.468~1.497 (3H, t, —CH₃), 1.537~1.893 (9H, m, cyclopentane), 2.281 (3H, s, —CH₃), 2.706~2.722 (2H, d, —CH₂—), 4.401~4.444 (2H, q, —CH₂—), 7.285~8.542 (9H, m, aromatic ring).

Mass spectrometry MS, m/Z: 523 (M+Na)⁺.

Examples 2~11

Referring to the method illustrated in Example 1, the compounds of Examples 2~11 were prepared from the corresponding reagents. The object compounds and ¹H-NMR data thereof were listed in Table 1.

TABLE 1

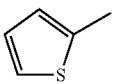

| Examples | Ar | R₁ | R₂ | R₃ | $^1$H-NMR δ[ppm] |
|---|---|---|---|---|---|
| 2 | 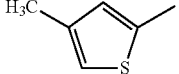 | n = 2, m = 4 | CH₂CH₃ | CH₃ | 1.132~1.170 (2H, m) 1.468 (3H, t) 1.543~1.901 (11H, m) 2.285 (3H, s) 2.701~2.732 (2H, t) 4.423 (2H, q) 7.285~8.563 (9H, m) |
| 3 | 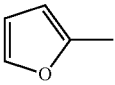 | n = 1, m = 3 | CH₂CH₃ | CH₃ | 1.455 (3H, t) 1.537~1.892 (9H, m) 2.285 (3H, s) 2.325 (3H, s) 2.711~2.731 (2H, d) 4.428 (2H, q) 7.486~8.552 (8H, m) |
| 4 | 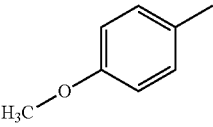 | n = 1, m = 3 | CH₂CH₃ | CH₃ | 1.465 (3H, t) 1.537~1.892 (9H, m) 2.290 (3H, s) 2.712~2.731 (2H, d) 4.450 (2H, q) 6.915~8.832 (9H, m) |
| 5 | 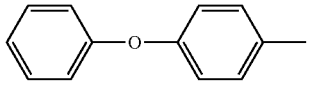 | n = 1, m = 3 | CH₂CH₃ | CH₃ | 1.466 (3H, t) 1.535~1.883 (9H, m) 2.284 (3H, s) 2.711~2.731 (2H, d) 3.907 (3H, s) 4.428 (2H, q) 7.091~8.798 (10H, m) |
| 6 | 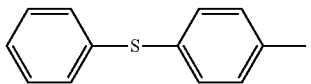 | n = 1, m = 3 | CH₂CH₃ | CH₃ | 1.454 (3H, t) 1.555~1.795 (9H, m) 2.284 (3H, s) 2.709~2.730 (2H, d) 4.428 (2H, q) 7.125~8.808 (15H, m) |
| 7 | 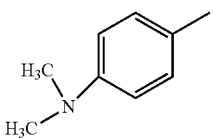 | n = 1, m = 3 | CH₂CH₃ | CH₃ | 1.514 (3H, t) 1.532~1.785 (9H, m) 2.285 (3H, s) 2.713~2.731 (2H, d) 4.453 (2H, q) 7.230~8.911 (15H, m) |
| 8 | 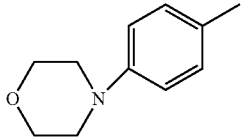 | n = 1, m = 3 | CH₂CH₃ | CH₃ | 1.463 (3H, t) 1.534~1.875 (9H, m) 2.279 (3H, s) 2.710~2.732 (2H, d) 3.067~3.419 (6H, m) 4.422 (2H, q) 6.803~8.910 (10H, m) |
| 9 | 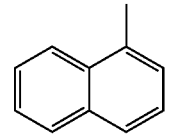 | n = 1, m = 3 | CH₂CH₃ | CH₃ | 1.458 (3H, t) 1.541~1.815 (9H, m) 2.288 (3H, s) 2.712~2.731 (2H, d) 3.187~3.659 (8H, m) 4.424 (2H, q) 6.865~8.532 (10H, m) |
| 10 | 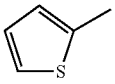 | n = 1, m = 3 | CH₂CH₃ | CH₃ | 1.408 (3H, t) 1.539~1.795 (9H, m) 2.235 (3H, s) 2.708~2.731 (2H, d) 4.453 (2H, q) 7.563~8.926 (13H, m) |
| 11 | 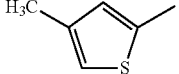 | n = 1, m = 4 | CH₂CH₃ | C₆H₆ | 1.468 (3H, t) 1.543~1.901 (11H, m) 2.711~2.733 (2H, d) 4.423 (2H, q) 7.285~8.563 (14H, m) |

Tests for Performance

By exemplifying the products in the Examples described above, the performances of the photoinitiator of this invention were tested, and were compared with the commercially available photoinitiator Irgacure369 (2-phenyl-2-dimethylamino-1-(-4-morpholinophenyl)-butanone-1), OXE-01 (1-(4-phenylthiophenyl)-octane-1,2-dione-2-benzoic acid oxime ester), and substance A (a ketoxime ester type photoinitiator (1-(4-phenylthiophenyl)-(3-cyclopentyl)-propan-1,2-dione-2-benzoic acid oxime ester) disclosed in CN101565472A).

1. Test for Violet Absorption Wavelength

Test method: 0.001 g of a photoinitiator product was accurately weighed and placed in a 100 mL volumetric flask, into which acetonitrile was added by the mark of 100 mL to formulate a solution with a concentration of $10^{-5}$ g/mL, and the violet absorption test was performed using a spectrophotometer. The test results were shown in Table 2.

TABLE 2

Violet Absorption Maximum

| Samples | Absorption Maximum (nm) |
|---|---|
| Example 1 | 366 |
| Example 2 | 365 |
| Example 4 | 358 |
| Example 6 | 376 |
| Example 9 | 384 |
| Example 11 | 370 |
| Irgacure 369 | 320 |
| OXE-01 | 326 |
| Substance A | 327 |

From the data in the above table, it can be seen that the carbazolyl ketoxime ester type photoinitiator illustrated in this invention has a longer violet absorption wavelength and is more easily to match a light source with a long wavelength, as compared with the conventional photoinitiators and current ketoxime ester type photoinitiators.

2. Test for Photosensitivity

Test method: A single tripropylene glycol diacrylate as a monomer was uniformly mixed with a single photoinitiator, and the obtained mixture was subjected to pedrail type exposure, wherein tripropylene glycol diacrylate:photoinitiator=50 g:2 g; the coating thickness was 24 μm; the lamp source was an LED lamp, the output wavelength was 390 nm, the power was 2 W/cm², and the magnitude of photosensitivity was judged by the times required to pass through the pedrail until the coated film was completely cured. The test results were shown in Table 3.

TABLE 3

The comparison of photosensitivity

| Samples | Times of Exposure |
|---|---|
| Example 1 | 2 |
| Example 4 | 2 |
| Example 9 | 2 |
| Example 11 | 3 |
| Irgacure 369 | >10 |
| OXE-01 | 8 |
| Substance A | 8 |

From the test results in Table 3, it can be obviously seen that the photoinitiator represented by the formula (I) disclosed by this invention exhibits a higher photosensitivity than Irgacure369, OXE-01, and substance A, under the irradiation of an LED lamp with a long wavelength output. That is, as a photoinitiator, the carbazole ketoxime ester type compound of this invention has more excellent photosensing (photo-curing) performance.

In summary, the carbazolyl ketoxime ester type photoinitiator of this invention has excellent application performance and extremely high photosensitive property, and in particular under the exposure lamp sources with low energy and long wavelength output such as LED, LDI, etc., and it exhibits very high sensitivity, which is obviously superior to the current photoinitiators such as commercially available Irgacure369, OXE-01, and the like, and is also superior to the carbazolyl ketoxime ester type photoinitiator disclosed in CN101565472A.

What is claimed is:

1. A carbazolyl ketoxime ester type photoinitiator, having a structure represented by the formula (I) of:

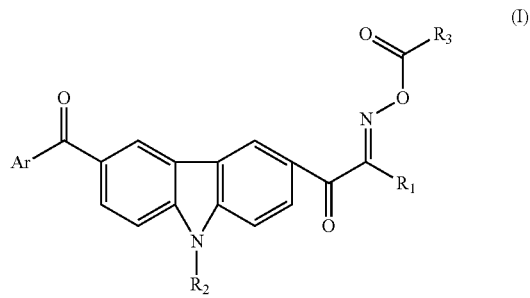

wherein, $R_1$ is

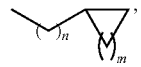

wherein n is 1 or 2, and m is 3 or 4, and wherein when n is 1, m is 3 or 4; or when n is 2, m is 4;

$R_2$ is a $C_1$-$C_5$ linear or branched alkyl group;

$R_3$ is a $C_1$-$C_3$ alkyl group;

Ar is furanyl or thienyl optionally substituted with one or more methyl or ethyl groups, or a substituted aryl group having an O, S, or N atom-containing substituent, provided that the substituent is not methoxy or ethoxy.

2. The carbazolyl ketoxime ester type photoinitiator according to claim 1, wherein, Ar is substituted aryl group having an O, S, or N atom-containing substituent selected from the group consisting of an alkylthio group, an alkylamino group, a piperazinyl group, and a morpholinyl group.

3. The carbazolyl ketoxime ester type photoinitiator according to claim 1, wherein $R_2$ is methyl, ethyl, n-propyl, or n-butyl.

4. The carbazolyl ketoxime ester type photoinitiator according to claim 1, wherein $R_3$ is methyl.

5. The carbazolyl ketoxime ester type photoinitiator according to claim 1, wherein Ar is :

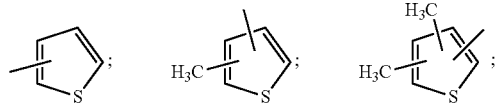

-continued

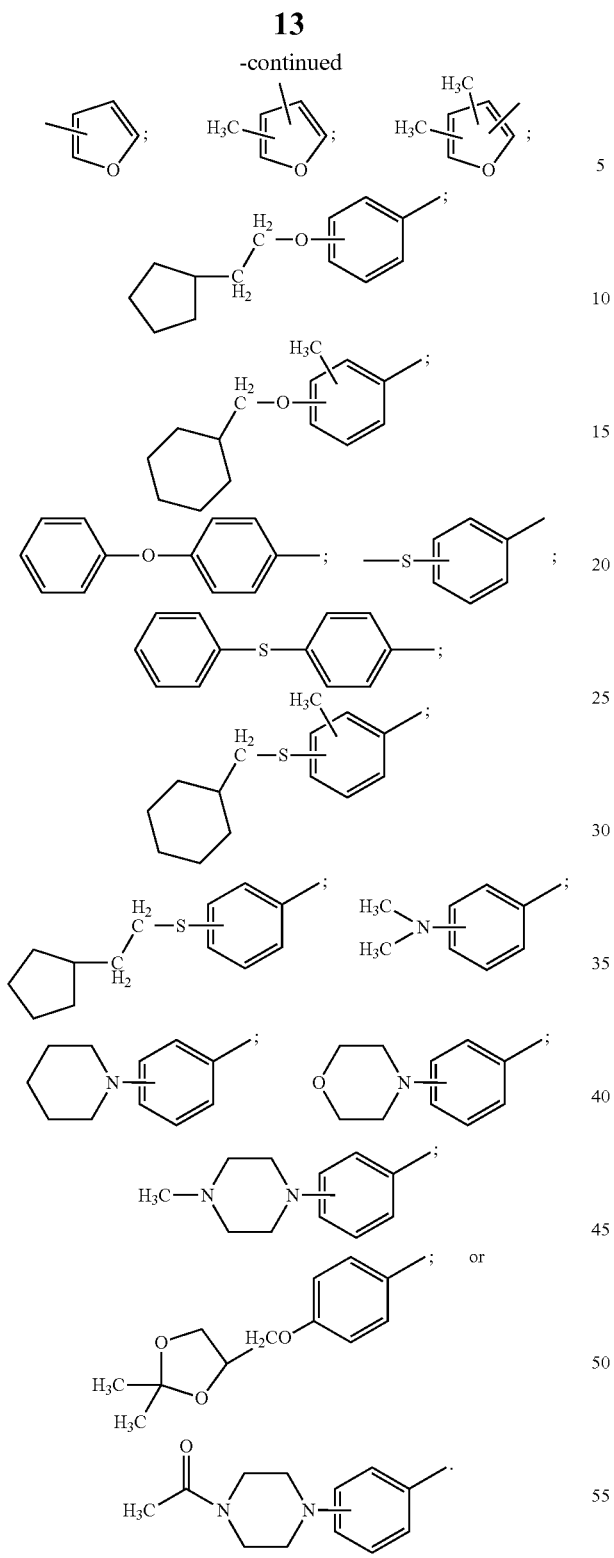

6. A method for preparing the carbazolyl ketoxime ester type photoinitiator according to claim 1, using carbazole as a starting raw material, and comprising the steps of:

(1) a substitution reaction, in which carbazole is dissolved in an organic solvent and is subjected to a substitution reaction with a bromoalkane $R_2$-Br to obtain an intermediate a, i.e., 9-$R_2$-carbazole, wherein the reaction process thereof is as follows:

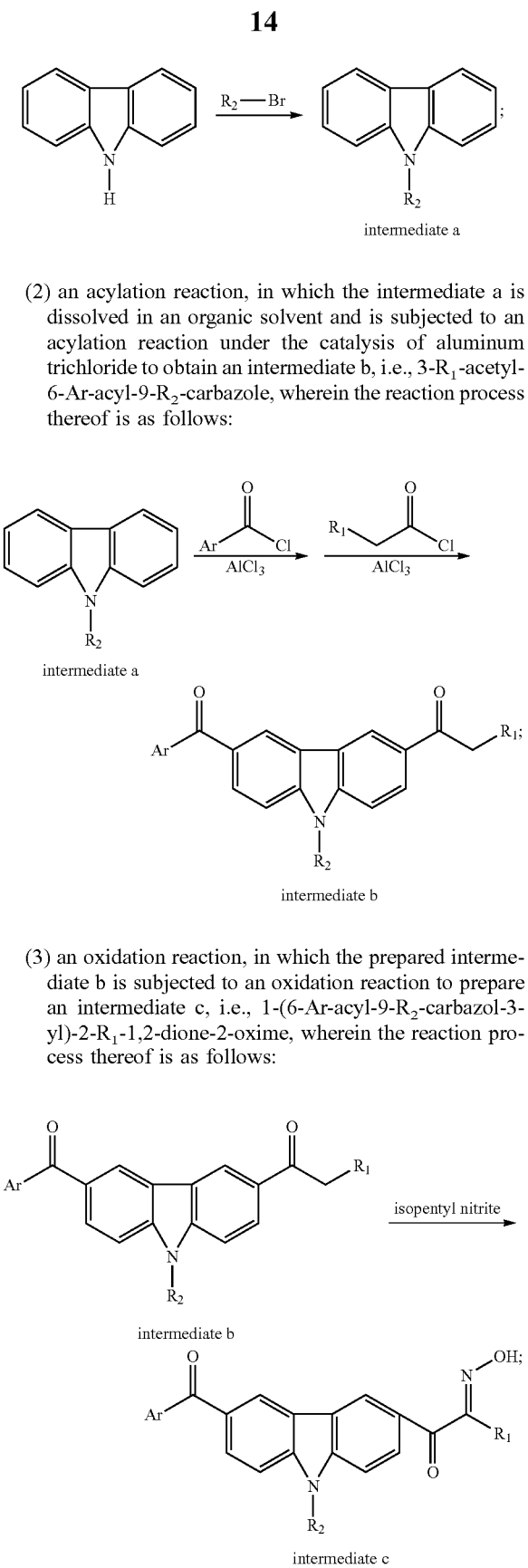

(2) an acylation reaction, in which the intermediate a is dissolved in an organic solvent and is subjected to an acylation reaction under the catalysis of aluminum trichloride to obtain an intermediate b, i.e., 3-$R_1$-acetyl-6-Ar-acyl-9-$R_2$-carbazole, wherein the reaction process thereof is as follows:

(3) an oxidation reaction, in which the prepared intermediate b is subjected to an oxidation reaction to prepare an intermediate c, i.e., 1-(6-Ar-acyl-9-$R_2$-carbazol-3-yl)-2-$R_1$-1,2-dione-2-oxime, wherein the reaction process thereof is as follows:

(4) an esterfication reaction, in which an esterfication reaction is performed between the prepared intermediate c and a $R_3$-formic anhydride or a $R_3$-formyl chloride to prepare the object product, i.e., the carbazolyl ketoxime ester type photoinitiator represented by the formula (I), wherein the reaction process thereof is as follows:
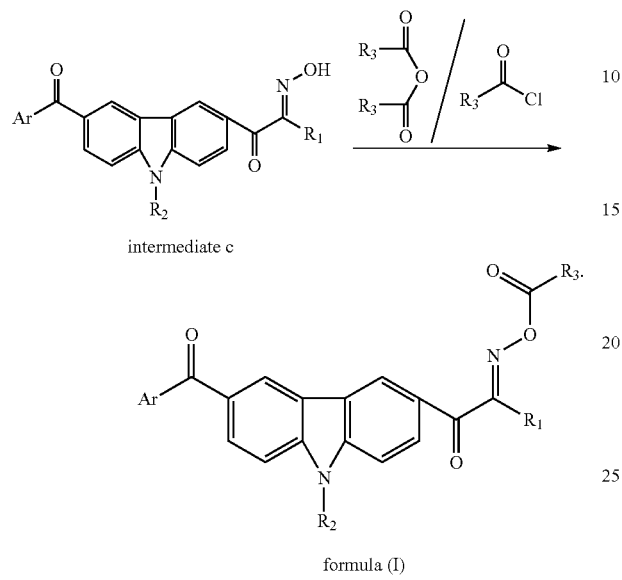
intermediate c
formula (I)
* * * * *